US006917687B2

(12) United States Patent
Vaishya

(10) Patent No.: US 6,917,687 B2
(45) Date of Patent: Jul. 12, 2005

(54) ACTIVE NOISE CONTROL USING A SINGLE SENSOR INPUT

(75) Inventor: Manish Vaishya, Rochester Hills, MI (US)

(73) Assignee: Siemens VDO Automotive Inc., Chatham (CA)

( * ) Notice: Subject to any disclaimer, the term of this patent is extended or adjusted under 35 U.S.C. 154(b) by 0 days.

(21) Appl. No.: 10/792,051

(22) Filed: Mar. 3, 2004

(65) Prior Publication Data

US 2004/0175003 A1 Sep. 9, 2004

Related U.S. Application Data

(60) Provisional application No. 60/453,120, filed on Mar. 7, 2003.

(51) Int. Cl.[7] ........................... A61F 11/06; H04B 1/00; G10K 11/16; H03B 29/00

(52) U.S. Cl. ........................................ 381/71.4; 381/86

(58) Field of Search .................................. 381/71.4, 86

(56) References Cited

U.S. PATENT DOCUMENTS

| | | | | | |
|---|---|---|---|---|---|
| 5,485,523 | A | * | 1/1996 | Tamamura et al. | 381/71.4 |
| 5,850,458 | A | * | 12/1998 | Tomisawa et al. | 381/71.4 |
| 6,688,422 | B2 | * | 2/2004 | Fuesser et al. | 181/206 |
| 2002/0038647 | A1 | * | 4/2002 | Tashiro et al. | 123/350 |

* cited by examiner

*Primary Examiner*—Xu Mei
*Assistant Examiner*—Devona E Faulk

(57) ABSTRACT

An active noise control system (20) includes a controller (34) that receives a signal from a single pressure sensor (36). The controller (34) estimates an engine speed of an engine (30) and a throttle position of a throttle valve associated with an air intake manifold (32). The controller (34) generates a noise control signal that drives a speaker (38), which responsively generates a noise attenuation signal. The disclosed embodiment may be used in an after-market product as it requires minimal interfacing with other vehicle electronics.

14 Claims, 1 Drawing Sheet

ACTIVE NOISE CONTROL USING A SINGLE SENSOR INPUT

CROSS REFERENCE TO RELATED APPLICATION

This application claims priority to U.S. Provisional Application No. 60/453,120 which was filed on Mar. 7, 2003.

BACKGROUND OF THE INVENTION

Active noise control systems are well known. One application for such system is on automotive vehicles. It is possible for engine noises to be propagated through the air intake manifold in a manner that they are heard in the passenger compartment of the vehicle. Typical active noise control systems include a speaker for generating a noise canceling signal. The speaker produces a sound that is out of phase with the engine noise to cancel out the noise to reduce the possibility for it being heard in the passenger compartment.

Typical active noise control systems require information from the vehicle engine for determining the control state and parameters and for computing the necessary speaker output in real time. When true cancellation is desired, very accurate information is required. Such information is acquired in some circumstances through the vehicle databus or by directly taking analog signals from various transducers.

The precise information for noise cancellation provides an indication abut the phase of the induction sound. Other vehicle parameters need to be predicted accurately, such as engine crank position, rotational speed, throttle opening, temperature, etc. The phase of the induction sound is sensitive to all such parameters.

At a minimum, the engine rotational speed and throttle opening position are required for any useful noise attenuation. Conventional systems rely upon at least two sensors for such information.

Accordingly, multiple inputs to the active noise control system typically are required. When analog signals are used, that adds cost and complexity to the system. When digital signals from the vehicle data bus are used, that adds complexity to the system. Either of these options require relatively significant interfacing with existing vehicle electronics.

Such noise control systems have not been able to be marketed in an after-market product because they require a significant interface with existing vehicle electronics. After-market products that require integrating with other vehicle electronics in that manner are not practical.

There is a need for a system that is not so complex or expensive. Additionally, it would be beneficial to provide a system that can be sold as an after-market product to provide noise control capabilities. This invention addresses that need while avoiding the shortcomings and drawbacks associated with typical systems.

SUMMARY OF THE INVENTION

In general terms, this invention is an active noise control system that relies upon a single sensor signal for estimating an engine speed and a throttle position that are used for generating a noise control signal. One embodiment is useful as an after-market system that can be easily installed on a vehicle not otherwise having a noise control system.

One example system includes a speaker for generating a noise attenuation signal. A controller controls the speaker with a control signal that corresponds to the noise attenuation signal. The controller uses a single pressure sensor signal to determine an estimated engine speed and an estimated throttle position. The controller generates the control signal based upon the estimated engine speed and the estimated throttle position.

In one example, the pressure signal has a frequency and the controller uses the frequency to determine the estimated engine speed. The sensor signal also has a DC component that is indicative of a mean air flow. The controller in one example uses the DC component of the sensor signal for determining the estimated throttle position. In one example, the controller uses the estimated engine speed and the DC component to determine the throttle position.

An example method of controlling an active noise control system includes generating an air flow signal using a pressure transducer. Estimating an engine speed from the air flow signal and estimating a throttle position from the same air flow signal provides information for generating a noise control signal.

The various features and advantages of this invention will become apparent to those skilled in the art from the following detailed description of the currently preferred embodiment. The drawings that accompany the detailed description can be briefly described as follows.

DETAILED DESCRIPTION OF THE PREFERRED EMBODIMENT

Figure 1:
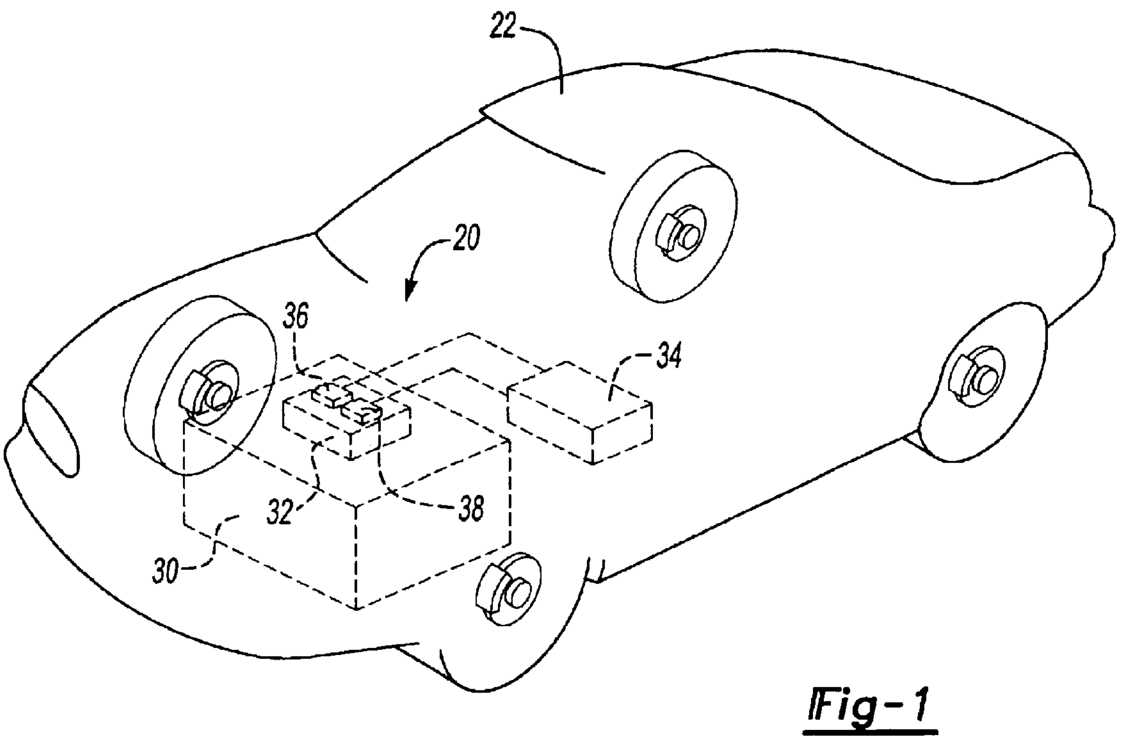
FIG. 1 schematically illustrates a vehicle incorporating an example embodiment of, an active noise control system.

FIG. 1 schematically shows an active noise control system 20 associated with a vehicle 22. An engine 30 has an air intake manifold 32 that includes a throttle valve (not illustrated) that operates responsive to an accelerator pedal position (not illustrated) in a known manner.

The active noise control system 20 includes a controller 34 that is adapted to be supported on the vehicle 22. A pressure sensor 36 is associated with the air intake manifold 32 in a manner such that it detects air flow through the manifold 32. The sensor 36 provides a signal, which is indicative of the sensed airflow, to the controller 34. In one example, the pressure sensor 36 is a transducer that is capable of measuring static and dynamic components of air pressure in the manifold 32. In one example, the sensor 36 is mounted in the path of the induction air flow so that the sensor output is responsive to pulsations caused by intake valve motion and the main air flow through the manifold duct.

In another example, the sensor 36 comprises a manifold absolute pressure (map) or a barometric atmospheric pressure sensor within the air flow path. One advantage to using a map sensor is that many vehicles already have one. In one example, the map sensor provides information regarding a vacuum pressure and has a sufficient dynamic range and frequency response (up to about 500 Hertz in one example) to satisfy the requirements of active noise control.

Figure 2:
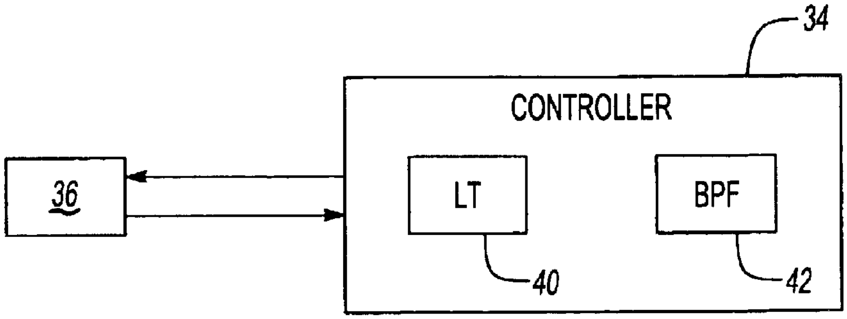
FIG. 2 schematically illustrates selected portions of an example controller used in an embodiment of this invention.

In the example of FIGS. 1 and 2, the controller 34 provides power to the sensor 36 so that a single connection to the controller 34 from the vehicle battery (not illustrated) provides all the power necessary for operating the controller 34 and the sensor 36.

Based upon the sensor signal, the controller 34 generates a noise control signal that drives a speaker 38 also associated with the intake manifold 32. The speaker 38 responsively generates a noise attenuation signal that is out of phase with the engine noise and, therefore, controls the amount of noise that may be propagated into the passenger compartment of the vehicle 22 or modifies the sound that is heard.

The controller 34 utilizes a single pressure sensor signal input to estimate an engine speed (i.e., RPM's) of the engine 30 and a throttle position of the throttle valve (not illustrated) associated with the manifold 32. The signal from the pressure sensor has a frequency and a DC component. The controller 34 estimates the engine speed based upon the pressure signal frequency. The controller 34 estimates the throttle valve position based upon the DC component of the sensor signal.

As shown in FIG. 2, a level-crossing trigger 40 is associated with the controller 34. The signal from the sensor 36 is converted into a digital signal for processing by the controller 34. The engine pulsations occur with every cylinder firing cycle. Therefore, applying the level crossing trigger 40 on the signal allows the controller 34 to derive the firing frequency and the engine rotational speed from the frequency of the signal. Known filtering techniques can be used to obtain a "cleaner" signal from the sensor 36.

The example of FIG. 2 also includes a band pass filter 42 for situations where signal distortion prevents the level-crossing trigger from working accurately. In one example, the band pass filter 42 is adjusted to cancel out frequencies in a selected range from an estimated frequency so that the exact frequency of the pressure signal can be determined. In one example, the controller 34 identifies a dominant order and uses that to estimate the engine speed.

In an example where the sensor 36 comprises a map sensor, the controller 34 uses the pulsation or frequency from the sensor signal, which is typically filtered out from the map sensor output because it is considered undesirable for conventional applications for estimating the engine speed. In other words, one example controller 34 uses a feature of a map sensor signal that is otherwise considered useless.

The controller 34 estimates the throttle position based upon the mean air flow through the manifold 32. A DC component of the pressure sensor signal is indicative of the mean air flow. Digital or analog filtering is used in one example to filter the pressure sensor signal to obtain the DC value.

The controller 34 in one example uses known relationships between air flow, throttle position and engine speed to estimate the throttle position. The estimated engine speed, which is derived from the frequency of the pressure signal as described above, and the DC component, which indicates the mean air flow, provide information to the controller 34 to use such known relationships to estimate the throttle position.

The controller 34 uses the estimated engine speed and estimated throttle position along with known techniques for generating the noise control signal. In one example, the controller 34 has a look up table indicating relationships between air flow, throttle position and engine RPM and another look up table with noise control signal values corresponding to estimated engine speeds and estimated throttle positions.

A disclosed embodiment may be used as an after-market noise control product for vehicles. Having a single sensor input to the controller eliminates the requirement for the controller 34 to interface with other vehicle electronics. In one example, the after-market product includes the pressure sensor 36 to be mounted in an appropriate position relative to the air intake manifold 32. In another example, the after-market product includes only the speaker 38 and the controller 34 and relies upon a signal from an existing manifold absolute pressure (MAP) sensor already on the vehicle. In either situation, a power amplifier, which can be powered through the controller, for driving the speaker allows for a single power connection to provide all necessary power from a vehicle battery for powering the controller 34, the sensor 36 and the speaker 38.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

I claim:

1. An active noise control system, comprising:

a speaker for generating a noise attenuation signal; and a controller that controls the speaker with a control signal corresponding to the noise attenuation signal, the controller using a single pressure signal indicative of airflow to determine an estimated engine speed and an estimated throttle position and generating the control signal based upon the estimated engine speed and the estimated throttle position.

2. The system of claim 1, including a pressure sensor that is adapted to be supported in a position to detect air flow in an air intake manifold, the pressure sensor providing the air pressure signal.

3. The system of claim 1, wherein the pressure signal has a frequency and wherein the controller uses the frequency to determine the estimated engine speed.

4. The system of claim 3, including a level crossing trigger and wherein the controller determines the estimated engine speed by identifying an engine firing frequency based upon processing the pressure signal using the level crossing trigger.

5. The system of claim 3, wherein the controller determines a dominant order from the pressure signal frequency and determines the engine speed based upon the dominant order.

6. The system of claim 3, including a band pass filter for filtering the pressure signal and wherein the controller uses the filtered signal to determine the engine speed.

7. The system of claim 1, wherein the pressure signal has a DC component and the controller uses the DC component to determine the estimated throttle position.

8. The system of claim 7, wherein the DC component is indicative of a mean airflow and the controller uses the DC component and the estimated engine speed to determine the estimated throttle position.

9. A method of controlling an active noise control system, comprising:

estimating an engine speed from a single air flow signal;

estimating a throttle position from the same air flow signal; and generating a noise control signal using the estimated engine speed and the estimated throttle position.

10. The method of claim 9, including estimating the engine speed using a frequency of the air flow signal.

11. The method of claim 10, including determining a dominant order from the frequency and estimating the engine speed based on the dominant order.

12. The method of claim 10, including estimating the frequency of the signal and filtering the signal to cancel out a selected range of frequencies near the estimated frequency and determining the frequency from the filtered signal.

13. The method of claim 9, including estimating the throttle position using a component of the air flow signal that indicates a mean air flow.

14. The method of claim 13, including estimating the throttle position using the air flow signal component and the estimated engine speed.

* * * * *